United States Patent [19]
Gorvin

[11] 3,933,807
[45] Jan. 20, 1976

[54] PREPARATION OF CYANOPHENOLS

[75] Inventor: John Henry Gorvin, London, England

[73] Assignee: Burroughs Wellcome Co., Research Triangle Park, N.C.

[22] Filed: Feb. 15, 1974

[21] Appl. No.: 442,912

Related U.S. Application Data
[63] Continuation of Ser. No. 255,186, May 19, 1972, abandoned.

[30] Foreign Application Priority Data
May 21, 1971  United Kingdom............. 16197/71

[52] U.S. Cl........ 260/243 A; 260/239.6; 260/239.7; 260/239.8; 260/247.1 R; 260/247.7 A; 260/247.7 K; 260/279 R; 260/283 R; 260/289 R; 260/293.73; 260/293.75; 260/293.77; 260/294.8 F; 260/294.9; 260/326.5 SF; 260/326.5 J; 260/329 R; 260/332.3 R; 260/335; 260/347.2; 260/347.8; 260/397.6; 260/456 P; 260/465 R; 260/465 D; 260/465 E; 260/465 F; 260/471 R; 260/521 R; 260/591; 260/592; 260/607 A; 424/248; 424/258; 424/263; 424/267; 424/274; 424/275; 424/285; 424/303; 424/304; 424/308; 424/317

[51] Int. Cl.²........................................ C07D 279/34

[58] Field of Search............. 260/326.5 SF, 326.5 J, 260/332.3 R, 347.2, 347.8, 465 D, 465 E, 465 F, 243 A, 279 R

[56] References Cited
OTHER PUBLICATIONS
Chemical Communications (1971) pp. 1120–1121 Gorvin.

*Primary Examiner*—Sherman D. Winters
*Attorney, Agent, or Firm*—Donald Brown

[57] ABSTRACT

A process for the preparation of a cyanophenol of formula (I)

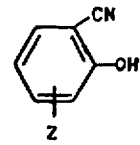

(I)

wherein Z is a substituent in the 4- or 6-position with respect to the hydroxy group, characterized in that cyanide ions are reacted in a dipolar aprotic solvent with a nitrobenzene of formula (II)

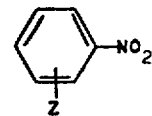

(II)

wherein Z has the same value as in formula (I) and is a group, other than a nitro group, known to withdraw electrons in substitution reactions and which does not contain a proton capable of ionizing under the defined reaction conditions if such ionization would inhibit the electron-withdrawing effect of the group Z.

In formula (I) and (II) the benzene ring is optionally substituted by one or more non electron-withdrawing groups, or by one or more electron-withdrawing groups provided that such electron-withdrawing groups are in positions other than the 4- and 6-positions with respect to the hydroxy group.

The compounds of formula (I) are of value in being readily hydrolysed to the corresponding salicylic acids of formula (III)

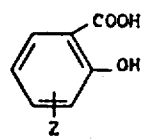

(III)

certain of which have been described in the literature as possessing a variety of pharmacological properties.

13 Claims, No Drawings

PREPARATION OF CYANOPHENOLS

This is a continuation of application Ser. No. 255,186, filed on May 19, 1972 now abandoned.

This invention relates to cyanophenols and their preparation and to their conversion to salicylic acids.

More particularly, the present invention relates to a novel process for the preparation of 2-cyanophenols of formula (I)

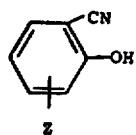

wherein Z is a substituent in the 4- or 6-position with respect to the hydroxy group and is a group, other than a nitro group, known to withdraw electrons in substitution reactions.

The novel process provided by the present invention for the preparation of the compounds of formula (I) comprises the reaction in a dipolar aprotic solvent of cyanide ions with a nitrobenzene of formula (II)

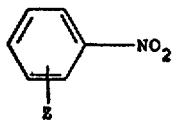

wherein Z has the same meaning as in formula (I). In the course of the reaction a substituent cyano group is attached to the benzene ring in the 2-position to that occupied by the nitro group, which latter is itself replaced by an hydroxy group.

Provided by formula (I) are those compounds wherein Z is a cyano group, a trifluoromethyl group, or a group Y.X— wherein X is the carbonyl or sulphonyl group and Y is a group which does not contain a proton capable of ionising under the conditions as herein described of the synthesis of the compounds if such ionization would inhibit the electron-withdrawing effect of the group X.

Thus Y may be
- a saturated aliphatic hydrocarbon group (for example an alkyl group such as a lower alkyl group having 1 to 4 carbon atoms);
- an alkoxy group (for example a lower alkoxy group having 1 to 4 carbon atoms, such as an ethoxy group);
- an aryloxy group (for example a phenoxy group);
- an aromatic nucleus (for example a phenyl or naphthyl group);
- a heteroaromatic nucleus (for example a xanthonyl, phenoxathiinyl, pyridyl furanyl, thienyl, N-(lower alkyl)pyrrolyl or quinolyl group);
- a disubstituted nitrogen atom (for example a pyrrolidino, piperidino or morpholino group, or a tertiary amino group such as a diarylamino, dialkylamino or N-alkyl-N-arylamino group where the "alkyl" is for example a lower alkyl having 1 to 4 carbon atoms and the "aryl" is for example phenyl); or
- a 5- or 6-membered non-aromatic cyclic or heterocyclic system having no proton ionizable in the manner defined above;

where Y is optionally joined to the benzene ring in formula (I) either directly or by a methylene, carbonyl, oxy, thio, sulphinyl or sulphonyl group, or by a monoalkylamino group where the "alkyl" is preferably a lower alkyl having 1 to 4 carbon atoms, and where Y, except when saturated aliphatic hydrocarbon, alkoxy or dialkylamino, is optionally substituted by one or more groups selected from
- halogen (chlorine, bromine, fluorine and iodine);
- aryl (for example phenyl, halogenophenyl, xylyl, salicyl and tolyl);
- aryloxy (for example phenoxy);
- alkoxy (for example lower alkoxy having 1 to 4 carbon atoms, such as methoxy, ethoxy, isopropoxy and butoxy);
- cyano;
- trifluoromethyl;
- and the groups —CO.W and —SO₂.W where W has the same meaning as Y as hereinabove defined, with the proviso that, when Y is N-alkyl-N-arylamino only the aryl moiety may be substituted in the above defined manner.

Further, in formulas (I) and (II) the benzene ring can optionally be further substituted by one or more non-electron withdrawing groups, such as halogen where the halogen is for example chlorine. As another possibility the benzene ring can optionally be substituted by one or more additional electron-withdrawing groups, such as those hereinbefore described, provided that said electron-withdrawing groups are in positions other than the 4- and 6-positions with respect to the hydroxy group.

As a preferred class within formula (I) are those compounds having no further substitution in the benzene ring and wherein Z is a cyano group or a group Y.X— wherein X is the carbonyl or sulphonyl group and Y is selected from N-phenyl-N-(lower alkyl)amino, furanyl, thienyl, N-(lower alkyl)pyrrolyl, cyclopentadienyl and phenyl, where the phenyl is optionally joined to the benzene ring in formula (I) either directly or by a methylene, carbonyl, thio, sulphinyl, sulphonyl, oxy or monoalkylamino group, and wherein Y is optionally substituted by one or more groups selected from halogen, aryl, aryloxy, alkoxy, cyano, trifluoromethyl and carboalkoxy, for example carbomethoxy and carboethoxy. The hydroxy-isophthalic acids corresponding to those compounds of formula (I) wherein Z is a cyano group have been described as possessing antipyretic and analgesic properties (Brit. J. Pharmacol., (1956), 11, 20; Nature(London), (1955), 175, 206. The salicylic acids and the salts thereof corresponding to the remainder of this preferred class of compounds within formula (I) have been described as possessing anti-inflammatory activity and as also showing analgesic, anti-fibrinolytic, anti-pyretic, diuretic and hypoglycaemic properties (Dutch Pat. Nos. 70.08621; 70.08622; 70.08627; 70.08628; 70.08629; 70.08631; 70.08636; and 70.08637).

As a second preferred class within formula (I) are those compounds having no further substitution in the benzene ring and wherein Z is a cyano group or a group Y.X— wherein X is the carbonyl or sulphonyl group and Y is selected from alkoxy, phenoxy, an aromatic nucleus, a heteroaromatic nucleus (a xanthonyl, phenoxathiinyl, pyridyl or quinolyl group) and a disubstituted nitrogen atom, wherein Y is optionally joined to the benzene ring in formula (I) either directly or by an oxy or monoalkylamino group, and wherein Y is optionally substituted by one or more groups selected from cyano, halogen, trifluoromethyl, aryl, phenoxy and alkoxy and the groups —CO.W and —SO₂.W where W has the same meaning as Y as hereinabove defined.

As a third preferred class within formula (I) are those compounds having no further substitution in the benzene ring and wherein Z is a cyano group or a group Y.X— wherein X is the carbonyl or sulphonyl group and Y is selected from N-phenyl-N-(lower alkyl)amino and phenyl, wherein the phenyl is optionally joined to the benzene ring in formula (I) either directly or by an oxy or monoalkylamino group, and wherein Y is optionally substituted by one or more groups selected from halogen, trifluoromethyl, aryl, phenoxy, alkoxy, cyano, and carboalkoxy, for example carbomethoxy and carboethoxy. The hydroxyisophthalic acids corresponding to those compounds of formula (I) wherein Z is a cyano group have been described as possessing antipyretic and analgesic properties (references as above) whilst the salicylic acids and the salts thereof corresponding to the remainder of this preferred class of compounds within formula (I) have been described as possessing anti-inflammatory activity and as also showing analgesic, anti-fibrinolytic, anti-pyretic, diuretic and hypoglycaemic properties (Dutch Pats. Nos. 70.08621; 70.08627; 70.08628; 70.08629; 70.08631; and 70.08636).

For the preparation of the compounds of formula (I) in the above-described manner the reagents are preferably anhydrous, this being especially critical where there are present in the compounds of formula (II) hydrolysable groups such as ester groups.

Suitable solvents include dimethylsulphoxide, dimethylformamide, hexamethylphosphoramide, dimethylacetamide, N-methyl-2-pyrrolidone, sulfolane, acetonitrile and mixtures thereof. The cyanide ions are conveniently provided by an ionisable cyanide salt which is also soluble in the solvent chosen, an alkali metal cyanide such as sodium cyanide or potassium cyanide being suitable.

It will be appreciated that the optimum reaction temperature will depend upon the particular compound of formula (II) concerned. Any temperature up to the reflux temperature of the reaction mixture may be employed but, having regard to this figure, a temperature of between 50° and 150°C, is preferred and a temperature of between 80° and 120°C. is most preferred.

In the course of the reaction azo and azoxy by-products are produced which may be readily removed during the purification of the cyanophenol.

As indicated above, certain of the salicylic acids of formula (III)

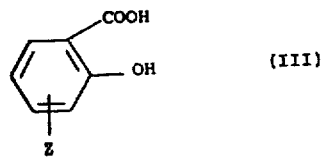

and the salts thereof, wherein Z has the same meaning as hereinabove, have been variously described as showing analgesic, anti-fibrinolytic, anti-inflammatory, anti-pyretic, diuretic and hypoglycaemic activity.

Heretofore, compounds of formula (III) and the salts thereof have been conventionally prepared by carboxylation of the corresponding phenol using carbon dioxide at high temperatures and superatmospheric pressures, and the phenol is itself generally prepared only by means of a multi-stage process. These disadvantages avoided if the compounds of formula (III) are prepared by hydrolysis of the cyanophenols of formula (I), the latter being obtained in the manner indicated above from the readily synthesised nitrobenzenes of formula (II). The hydrolysis may be effected under either acid or alkaline conditions; for acid hydrolysis 60% sulphuric acid or a hydrohalide acid such as concentrated hydrochloric acid is a suitable agent, and for alkaline hydrolysis an aqueous alkali such as 25% aqueous sodium hydroxide may be used. The compounds of formula (III) may be isolated either as such or as a salt thereof.

The present invention therefore provides a process as hereinbefore described for the preparation of the compounds of formula (I), the novel compounds of formula (I), the known compounds of formula (I) when prepared by the process as hereinbefore described, a process as hereinbefore described for preparing the compounds of formula (III) and the salts thereof from the compounds of formula (I), and the compounds of formula (III) and the salts thereof when so prepared.

The following Examples illustrate the present invention, all temperatures being in degrees Celsius.

EXAMPLE 1 a. A mixture of dry powdered potassium cyanide (4g.) and 4-nitrobenzophenone (2.27g) was suspended in dimethylsulphoxide (40 ml.) and heated for 4 hours at 100°C. with occasional agitation. The solution was then poured into water and the insoluble neutral fraction removed by filtration. After acidification the filtrate was extracted with ether and the 5-benzoylsalicylonitrile thus obtained was crystallised from aqueous ethanol to give needles, m.p. 185°–186°C.

b. By a similar method 4-methoxy-4'-nitrobenzophenone was converted into 5-p-methoxybenzoylsalicylonitrile, m.p. 167°–168°C. (after loss of one molecule of water of hydration).

EXAMPLE 2 a. A mixture of p-nitrodiphenylsulphone (13.2g.) and dry powdered potassium cyanide (10g.) in dimethylsulphoxide (100 ml.) was heated for 3½ hours at 100°C. The solution was diluted with a large volume of water and the precipitate collected by filtration. This solid was treated with a mixture of 10% aqueous sodium hydroxide (200 ml.) and 10% aqueous sodium carbonate (50 ml.) and the insoluble solid filtered off. On acidification of the filtrate with hydrochloric acid there was obtained 5-benzenesulphonylsalicylonitrile which gave hydrated crystals (from ethanol), m.p. 195°–196°C.

b. By a similar procedure 4-chloro-4'-nitrodiphenylsulphone was converted to 5-p-chlorobenzenesulphonylsalicylonitrile, which formed hydrated crystals (from ethanol) m.p. 92°C. and 205°–207°C.

EXAMPLE 3 a. A mixture of 3-nitroxanthone (1.44g.) and powdered potassium cyanide (3.0g.) in dimethylformamide (50ml.) was heated at 100°C. for 4 hours, after which time water was added and the insoluble precipitate removed. Acidification gave 3-hydroxyxanthone-4-carbonitrile which from aqueous ethanol gave crystals containing one molecule of water of crystallisation and having m.p. 304°–305°C.

b. In a similar manner N-methyl-3-nitroacridone was converted to 3-hydroxy-N-methylacridone-4-carbonitrile (m.p. 310°C.).

EXAMPLE 4 a. p-Nitrobenzonitrile (14.8g.) was heated at 100°C. in dimethylsulphoxide (70 ml.) with dry powdered potassium cyanide (20g.) for 2 hours. The mixture was poured into water and an insoluble precipitate removed. Acidification of the filtrate and extraction with ether gave 2,4-dicyanophenol (did not melt but changed form at 240°C.); on hydrolysis with concentrated hydrochloric acid this compound gave 4-hydroxyisophthalic acid, m.p. 310°C.

a. Similarly, from o-nitrobenzonitrile was prepared 2,6-dicyanophenol which on hydrolysis with concentrated hydrochloric acid gave 2-hydroxyisophthalic acid, m.p. (monohydrate) 245°C.

EXAMPLE 5 a. Ethyl p-nitrobenzoate (1.95g.) was heated in dimethylsulphoxide (15 ml.) with dry powdered potassium cyanide (2g.) at 110°–120°C. for 3½ hours. The solution was poured into water and acidified. The filtered solid was shaken with 10% aqueous sodium carbonate containing some sodium hydroxide, filtered and acidified. The crystals obtained on standing were recrystallised from hot water to give ethyl 3-cyano-4-hydroxybenzoate, m.p. 192°–193°C., which was hydrolysed with concentrated hydrochloric acid to yield 4-hydroxyisophthalic acid, m.p. 310°C.

b. By treating N-p-nitrobenzoylpiperidine in a similar manner was obtained N-(3-cyano-4-hydroxybenzoyl)-piperidine, which on hydrolysis with concentrated hydrochloric acid gave 4-hydroxyisophthalic acid, m.p. 310°C.

EXAMPLE 6

4-p-Nitrobenzoyl)pyridine (cf.Bryans and Pyman, J. Chem. Soc., 1929, 552) (1.04g.) was heated with potassium cyanide (1.0g.) in dimethylsulphoxide (20 ml.) at 100°C. for 3½ hours. The solution was poured into water and the precipitated material removed by addition of charcoal and filtration of the suspension through kieselguhr. The filtrate was neutralized (pH 6-7) and the precipitated solid collected. Crystallisation from ethanol gave 4-(3-cyano-4-hydroxybenzoyl)pyridine, m.p. 310°–311°C.

EXAMPLE 7

2-p-Nitrobenzoylthiophene (2.33 g.) was allowed to react with potassium cyanide (3.9 g., 6 mols) in dimethyl sulphoxide (40 ml.) at 100°C for 3½ hours. The solution was poured into water and the cloudiness removed with charcoal. The clear filtrate gave a precipitate on acidification; this was collected and crystallised from aqueous ethanol to give 2-(3-cyano-4-hydroxybenzoyl)thiophene, m.p. 216°C.

EXAMPLE 8

2-Nitro-α,α,α-trifluorotoluene (3.82 g.) was heated at 100°C for 3 hours with potassium cyanide (7.8 g.) in dimethyl sulphoxide (40 ml.). After pouring into water, the mixture was brought to pH 7 and filtered. Acidification, ether extraction, and removal of the ether gave a solid which was sublimed or crystallised from aqueous ethanol to give 3-trifluoromethyl-salicylonitrile, m.p. 134°C.

EXAMPLE 9

Using a method similar to that of Example 1, 3-chloro-4-nitrobenzophenone was converted by potassium cyanide in dimethyl sulphoxide into 3-chloro-5-benzoylsalicylonitrile, which crystallised from aqueous ethanol as the monohydrate, m.p. 120°C.

EXAMPLE 10

Using a method similar to that of Example 5, p-nitroacetophenone was converted by treatment with potassium cyanide in dimethyl sulphoxide into 5-acetylsalicylonitrile, which gave crystals, m.p. 178°C., from aqueous ethanol [Borsche and Hahn-Weinheimer, *Annalen*, 1950, 570, 155, prepared this compound by the acetylation of salicylonitrile, but gave m.p. 78°].

What we claim is:

1. In a process for the preparation of the compound of formula (I)

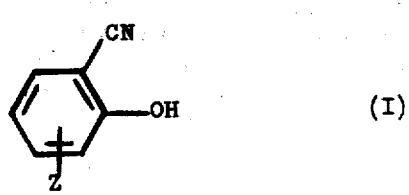

wherein Z is a substituent in the 4- or 6-position with respect to the hydroxy group and is selected from a cyano group and a group Y.X —, wherein X is selected from the carbonyl group and the sulphonyl group and Y is selected from N-phenyl-N-(lower alkyl) amino, furanyl, thienyl, N-(lower alkyl) pyrrolyl, cyclopentadienyl and phenyl, where the phenyl may be joined at the 2-position thereof with respect to X to the benzene ring in formula (I) at a position therein adjacent X either by a bond or by a methylene, carbonyl, thio, sulphinyl, sulphonyl, oxy or monoalkylamino group, and wherein Y is optionally substituted by one or more groups selected from halogen, aryl which is selected from the group consisting of phenyl, halogenophenyl, xylyl, salicyl and tolyl, phenoxy lower alkoxy, cyano, trifluoromethyl and carboloweralkoxy and wherein lower alkyl and alkoxy herein have 1 to 4 carbon atoms provided that when Y is N-phenyl-N-(lower alkyl) amino only the phenyl moiety may be substituted; and wherein in the compound of formula (I) there is no other substituent in the benzene ring, which comprises reacting cyanide ions in dipolar aprotic solvent with a nitrobenzene of formula (II)

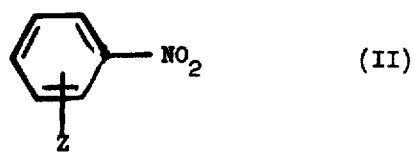

wherein Z is a substituent in the 4- or 6-position with respect to the nitro group and is defined as above.

2. In a process for the preparation of the compound of formula (I)

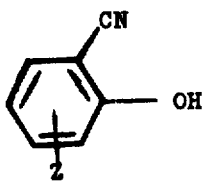

(I)

wherein Z is a substituent in the 4- or 6-position with respect to the hydroxy group and is selected from a cyano group and a group Y.X — wherein X is selected from the carbonyl group and the sulphonyl group and Y is selected from N-phenyl-N-(lower alkyl) amino and phenyl, where the phenyl may be joined at the 2-position thereof with respect to X to the benzene ring in formula (I) at a position therein adjacent X either by a bond or by an oxy or monoalkylamino group, and wherein in each instance the phenyl moiety is optionally substituted by one or more groups selected from halogen, trifluoromethyl, aryl which is selected from the group consisting of phenyl, halogenophenyl, xylyl, salicyl and tolyl, phenoxy, lower alkoxy, cyano, and carboloweralkoxy and wherein the lower alkyl and alkoxy herein have 1 to 4 carbon atoms; and wherein that in the compound of formula (I) there is no other substituent in the benzene ring, which comprises reacting cyanide ions in a dipolar aprotic solvent with a nitrobenzene of formula (II)

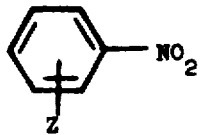

(II)

wherein Z is a substituent in the 4- or 6-position with respect to the nitro group and is defined as above.

3. A process as claimed in claim 1, characterized in that the reagents are anhydrous.

4. A process as claimed in claim 1, characterized in that the dipolar aprotic solvent is selected from the group consisting of dimethylsulphoxide, dimethylformamide, hexamethylphosphoramide, dimethylacetamide, N-methyl-2-pyrrolidone, sulfolane, acetonitrile and mixtures thereof.

5. A process as claimed in claim 1, characterized in that the reaction is effected at a temperature of between 50° and 150°C.

6. The process of claim 1 wherein Z is selected from a cyano group and a group Y.X— wherein X is selected from the carbonyl group and the sulphonyl group and Y is selected from thienyl, and phenyl, where the phenyl may be joined to the benzene ring in formula I by an oxy or monoalkylamino group and wherein Y is optionally substituted by one or more groups selected from halogen and alkoxy.

7. The process of claim 6 wherein the final product of formula I is precipitated from water.

8. The process of claim 2 wherein Z is selected from a cyano group and a group Y.X — wherein X is selected from the carbonyl group and the sulphonyl group and Y is selected from a phenyl, where the phenyl may be joined to the benzene ring formula I by an oxy or monoalkylamino group, and wherein the phenyl moiety is optionally substituted by one or more groups selected from halogen and alkoxy.

9. The process of claim 8 wherein the final product of formula I is precipitated from water.

10. The method of claim 2 characterized in that the reagents are anhydrous.

11. The method of claim 2 characterized in that the dipolar solvent is selected from the group consisting of dimethylsulphoxide, dimethylformamide, hexamethylphosphoramide, dimethylacetamide, N-methyl-2-pyrrolidone, sulfolane, acetonitrile and mixtures thereof.

12. The method of claim 2 characterized in that the reaction is effected at a temperature of between 50° and 150°C.

13. The method of claim 1 in which carboloweralkoxy is selected from the group consisting of carbomethoxy and carboethoxy.

* * * * *